United States Patent
Stigall et al.

(10) Patent No.: US 11,559,207 B2
(45) Date of Patent: Jan. 24, 2023

(54) ROTATIONAL INTRAVASCULAR DEVICES, SYSTEMS, AND METHODS UTILIZING PHOTOACOUSTIC AND ULTRASOUND IMAGING TECHNIQUES

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 761 days.

(21) Appl. No.: 16/088,104

(22) PCT Filed: Mar. 23, 2017

(86) PCT No.: PCT/IB2017/051679
§ 371 (c)(1),
(2) Date: Sep. 25, 2018

(87) PCT Pub. No.: WO2017/168289
PCT Pub. Date: Oct. 5, 2017

(65) Prior Publication Data
US 2020/0297214 A1   Sep. 24, 2020

Related U.S. Application Data

(60) Provisional application No. 62/315,251, filed on Mar. 30, 2016.

(51) Int. Cl.
A61B 5/00 (2006.01)
A61B 8/12 (2006.01)
A61B 8/00 (2006.01)

(52) U.S. Cl.
CPC .......... *A61B 5/0095* (2013.01); *A61B 5/6852* (2013.01); *A61B 8/12* (2013.01);
(Continued)

(58) Field of Classification Search
USPC ........................................................ 600/407
See application file for complete search history.

(56) References Cited

U.S. PATENT DOCUMENTS

| | | |
|---|---|---|
| 2009/0253989 A1 | 10/2009 | Caplan |
| 2010/0179434 A1 | 7/2010 | Thornton |

(Continued)

FOREIGN PATENT DOCUMENTS

| | | |
|---|---|---|
| JP | 2013022171 A | 2/2013 |
| JP | 2013027482 A | 2/2013 |

(Continued)

*Primary Examiner* — Amanda Lauritzen Moher
*Assistant Examiner* — Renee C Langhals

(57) ABSTRACT

Imaging devices, systems, and methods are provided. Some embodiments of the present disclosure are particularly directed to imaging a region of interest in tissue with photoacoustic and ultrasound modalities. In some embodiments, a medical sensing system (100) includes a measurement apparatus (102) configured to be placed within a vascular pathway. The measurement apparatus may include a sensor array (106) comprising two or more sensor modalities. The sensor array may be configured to receive sound waves created by the interaction between emitted optical pulses and tissue, transmit and receive ultrasound signals, and rotate around a longitudinal axis of the measurement device. The medical sensing system may also include a processing engine operable to produce images of the region of interest and a display configured to visually display the image of the region of interest.

20 Claims, 4 Drawing Sheets

(52) U.S. Cl.
CPC .......... *A61B 8/4461* (2013.01); *A61B 5/0035* (2013.01); *A61B 8/4416* (2013.01); *A61B 8/4494* (2013.01)

(56) References Cited

U.S. PATENT DOCUMENTS

| | | | | |
|---|---|---|---|---|
| 2012/0197113 | A1* | 8/2012 | Courtney | A61B 8/14 600/447 |
| 2013/0338498 | A1* | 12/2013 | Emelianov | A61B 8/12 600/431 |
| 2014/0180056 | A1* | 6/2014 | Hoseit | A61B 8/4483 600/407 |
| 2014/0221842 | A1* | 8/2014 | Castelino | A61B 5/0035 600/459 |

FOREIGN PATENT DOCUMENTS

| | | | | |
|---|---|---|---|---|
| WO | 2010080991 | A2 | 7/2010 | |
| WO | WO-2010080776 | A1 * | 7/2010 | ........... A61B 5/0084 |

\* cited by examiner

ROTATIONAL INTRAVASCULAR DEVICES, SYSTEMS, AND METHODS UTILIZING PHOTOACOUSTIC AND ULTRASOUND IMAGING TECHNIQUES

This application is the U.S. National Phase application under 35 U.S.C. § 371 of International Application No. PCT/IB2017/051679, filed on Mar. 23, 2017, which claims the benefit of Provisional Application Ser. No. 62/315,251, filed Mar. 30, 2016. These applications are hereby incorporated by reference herein.

TECHNICAL FIELD

The present disclosure relates generally to imaging and mapping vascular pathways and surrounding tissue with photoacoustic and ultrasound modalities.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible measurement apparatus such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy.

For example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. In side-looking rotational devices, the transducer element is oriented such that the ultrasound beam propagates generally perpendicular to the longitudinal axis of the device. In forward-looking rotational devices, the transducer element is pitched towards the distal tip so that the ultrasound beam propagates more towards the tip (in some devices, being emitted parallel to the longitudinal centerline). The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS medical sensing system may assemble a two dimensional display of the tissue, vessel, heart structure, etc. from a sequence of pulse/acquisition cycles occurring during a single revolution of the transducer. In order to image a length of a vessel, the transducer element may be drawn through the vessel as it spins.

In contrast, solid-state IVUS devices utilize a scanner assembly that includes an array of ultrasound transducers connected to a set of transducer controllers. In side-looking and some forward-looking IVUS devices, the transducers are distributed around the circumference of the device. In other forward-looking IVUS devices, the transducers are a linear array arranged at the distal tip and pitched so that the ultrasound beam propagates closer to parallel with the longitudinal centerline. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the medical sensing system with a simple electrical cable and a standard detachable electrical connector. While the transducers of the scanner assembly do not spin, operation is similar to that of a rotational system in that, in order to image a length of a vessel, the scanner assembly is drawn through the vessel while stepping through the transmit-receive sets to produce a series of radial scans.

Rotational and solid-state state IVUS are merely some examples of imaging modalities that sample a narrow region of the environment and assemble a two- or three-dimensional image from the results. Other examples include optical coherence tomography (OCT), which has been used in conjunction with ultrasound systems. One of the key challenges using these modalities with in a vascular pathway is that they are limited in gathering data on anatomy beyond the vessel walls. Although OCT imaging may yield higher resolution than IVUS imaging, OCT has particularly limited penetration depth and may take more time to image a region of tissue.

Another recent biomedical imaging modality is photoacoustic imaging. Photoacoustic imaging devices deliver a short laser pulse into tissue and monitor the resulting acoustic output from the tissue. Due to varying optical absorption throughout the tissue, pulse energy from the laser pulse causes differential heating in the tissue. This heating and associated expansion leads to the creation of sound waves corresponding to the optical absorption of the tissue. These sound waves can be detected and an image of the tissue can be generated through analysis of the sound waves and associated vascular structures can be identified, as described in U. S. Patent Publication 2013/0046167 titled "SYSTEMS AND METHODS FOR IDENTIFYING VASCULAR BORDERS," which is hereby incorporated by reference in its entirety.

Accordingly, for these reasons and others, the need exists for improved systems and techniques that allow for the mapping of vascular pathways and surrounding tissue.

SUMMARY

Embodiments of the present disclosure provide a mapping system that combines photoacoustic and IVUS imaging system on a measurement apparatus configured to be placed in a vascular pathway. The sensor array may be rotatable around an axis of the measurement apparatus, allowing the system to map vascular pathways and surrounding tissue.

In some embodiments, a medical sensing system is provided comprising: an elongate body sized and shaped for insertion into a vascular pathway; a rotational drive member extending along a length of the elongate body; an optical emitter coupled to a distal portion of the rotational drive member, the optical emitter configured to emit optical pulses to tissue in a region of interest; and a measurement apparatus coupled to the distal portion of the rotational drive member, the measurement apparatus configured to: receive sound waves generated by the tissue as a result of interaction of the optical pulses with the tissue; transmit ultrasound signals; and receive ultrasound echo signals based on the transmitted ultrasound signals.

In some embodiments, the system further comprises a processing engine in communication with the measurement apparatus, the processing engine operable to produce an image of the region of interest based on the received sound waves and the received ultrasound echo signals. The system may include a display in communication with the processing engine, the display configured to visually display the image of the region of interest. The drive member may be configured to rotate the optical emitter around a longitudinal axis of the measurement apparatus. In some embodiments, the optical emitter is in communication with an external optical source. An optical fiber may connect the measurement apparatus and the external optical source.

In some embodiments, the measurement apparatus comprises at least one ultrasound transducer configured to transmit the ultrasound signals and receive the ultrasound echo signals based on the transmitted ultrasound signals. The at least one ultrasound transducer may be further configured to receive the sound waves generated by the tissue as a result of interaction of the optical pulses with the tissue. In some embodiments, the at least one ultrasound transducer is configured to alternate in receiving sound waves and ultrasound echo signals. The measurement apparatus may further comprise at least one photoacoustic transducer configured to receive sound waves generated by the tissue as a result of interaction of the optical pulses with the tissue. In some embodiments, the at least one photoacoustic transducer and the at least ultrasound transducer are configured to alternate in receiving sound waves and ultrasound echo signals.

In some embodiments, a medical sensing system is provided comprising: an optical source configured to emit optical pulses; an intravascular device in communication with the optical source; the intravascular device including: a rotational drive member extending along a length of the elongate body; an optical emitter coupled to a distal portion of the rotational drive member, the optical emitter configured to emit optical pulses received from the optical source to tissue in a region of interest; and a measurement apparatus coupled to the distal portion of the rotational drive member, the measurement apparatus configured to: receive sound waves generated by the tissue as a result of interaction of the optical pulses with the tissue; transmit ultrasound signals; and receive ultrasound echo signals based on the transmitted ultrasound signals; a processing engine in communication with the intravascular device, the processing engine operable to produce an image of the region of interest based on the received sound waves and the received ultrasound echo signals; and a display in communication with the processing engine, the display configured to visually display the image of the region of interest.

In some embodiments, the drive member is configured to rotate the optical emitter around a longitudinal axis of the measurement apparatus. The system may comprise an optical fiber extending between the intravascular device and the optical source. The system may comprise a controller operable to control the operation of the optical source and rotation of the drive member. In some embodiments, the measurement apparatus comprises at least one ultrasound transducer configured to transmit ultrasound signals and receive ultrasound echo signals based on the transmitted ultrasound signals.

In some embodiments, the at least one ultrasound transducer is further configured to receive sound waves generated by the tissue as a result of interaction of the optical pulses with the tissue. Furthermore, the at least one ultrasound transducer may be configured to alternate in receiving sound waves and ultrasound echo signals. The measurement apparatus may further comprise at least one photoacoustic transducer configured to receive sound waves generated by the tissue as a result of interaction of the optical pulses with the tissue.

In some embodiments, a method of mapping a region of interest is provided, comprising: transmitting, with a laser emitter of an intravascular device positioned within a vascular pathway of a region of interest, focused laser pulses on tissue in the region of interest; receiving, with at least one photoacoustic sensor of the intravascular device positioned within the vascular pathway of the region of interest, sound waves generated by the interaction of the focused laser pulses with the tissue; rotating at least one of the laser emitter and the at least one photoacoustic sensor about a longitudinal axis of the intravascular device; producing an image of the region of interest based on the received sound waves; and outputting the image of the region of interest to a display.

In some embodiments, the method further comprises: transmitting, with at least one ultrasound transducer of the intravascular device positioned within the vascular pathway of the region of interest, ultrasound signals toward the tissue in the region of interest; and receiving, with the at least one ultrasound transducer of the intravascular device positioned within the vascular pathway of the region of interest, ultrasound echo signals of the transmitted ultrasound signals. The step of producing an image of the region of interest may be based on the received sound waves and the received ultrasound echo signals.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1A:
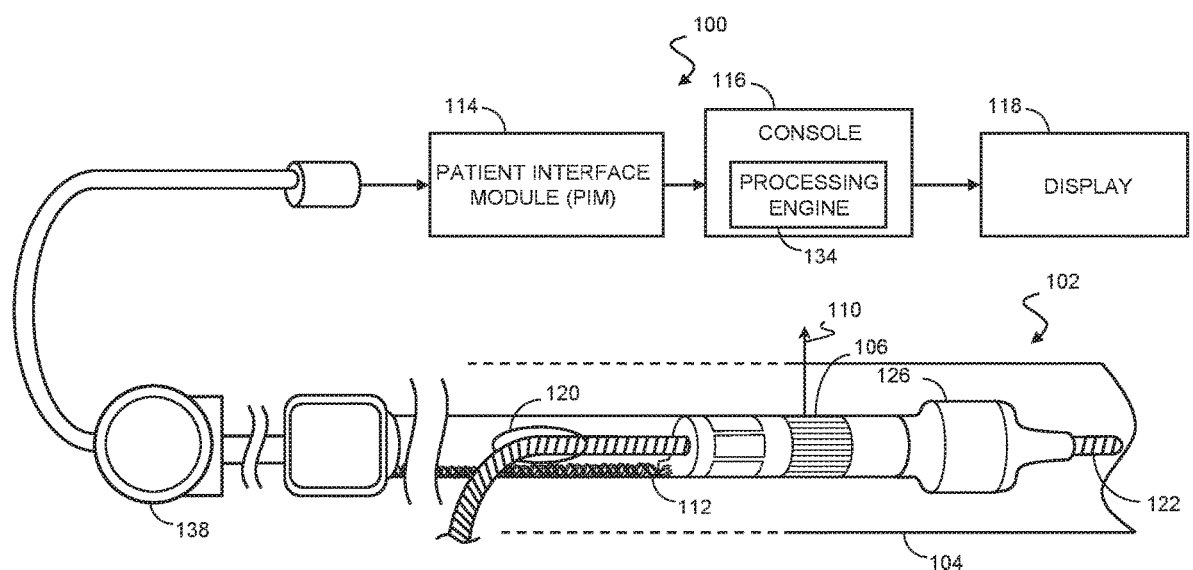
FIG. 1A is a diagrammatic schematic view of a medical sensing system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the intravascular sensing system is described in terms of cardiovascular imaging, it is understood that it is not intended to be limited to this application. The system is equally well suited to any application requiring imaging within a lumen or cavity of a patient. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A is a diagrammatic schematic view of a medical sensing system 100 according to some embodiments of the present disclosure. The medical sensing system 100 includes a measurement apparatus 102 (such as a catheter, guide wire, or guide catheter). As used herein, "measurement apparatus" or "flexible measurement apparatus" includes at least any thin, long, flexible structure that can be inserted into the vasculature of a patient. While the illustrated embodiments of the "measurement apparatus" of the present disclosure have a cylindrical profile with a circular cross-sectional profile that defines an outer diameter of the flexible measurement apparatus 102, in other instances, all or a portion of the flexible measurement apparatus 102 may have other geometric cross-sectional profiles (e.g., oval, rectangular, square, elliptical, etc.) or non-geometric cross-sectional profiles. Flexible measurement apparatus 102 may include, for example, guide wires, catheters, and guide catheters. In that regard, a catheter may or may not include a lumen extending along all or a portion of its length for receiving and/or guiding other instruments. If the catheter includes a lumen, the lumen may be centered or offset with respect to the cross-sectional profile of the device.

The medical sensing system 100 may be utilized in a variety of applications and can be used to assess vascular pathways and structures within a living body. To do so, the measurement apparatus 102 is advanced into a vascular passage 104. The vascular passage 104 represents fluid filled or surrounded structures, both natural and man-made, within a living body that may be imaged and can include for example, but without limitation, structures such as: organs including the liver, heart, kidneys, as well as valves within the blood or other systems of the body. In addition to imaging natural structures, the images may also include man-made structures such as, but without limitation, heart valves, stents, shunts, filters and other devices positioned within the body. The measurement apparatus 102 includes one or more sensors 106 disposed along the length of the apparatus 102 to collect diagnostic data regarding the vascular pathway 104. In various embodiments, the one or more sensors 106 correspond to sensing modalities such as IVUS imaging, pressure, flow, OCT imaging, transesophageal echocardiography, temperature, other suitable modalities, and/or combinations thereof.

In the exemplary embodiment of FIG. 1A, the measurement apparatus 102 includes a solid-state IVUS device, and the sensors 106 include one or more IVUS ultrasound transducers and/or photoacoustic transducers and associated control. As used herein, a "photoacoustic transducer" includes at least a sensor configured to detect photoacoustic waves generated as a result of the interaction of optical pulses with tissue. In one embodiment, a photoacoustic transducer utilizes the same ultrasound detection mechanism as an IVUS ultrasound transducer. In some implementations, a single transducer can serve as both an IVUS transducer and a photoacoustic transducer. In another embodiment, a photoacoustic transducer uses a dedicated photoacoustic wave detection mechanism distinct from that of an IVUS ultrasound transducer. In another embodiment, a photoacoustic transducer uses a dedicated photoacoustic wave detection mechanism distinct from that of an IVUS ultrasound transducer. The system of FIG. 1A may include aspects of phased-array IVUS devices, systems, and methods associated with the Eagle Eye® Platinum catheter available from Volcano Corporation as well as those described in U.S. Pat. No. 7,846,101 and/or U.S. patent application Ser. No. 14/812,792, filed Jul. 29, 2015, each of which is hereby incorporated by reference in its entirety.

The sensors 106 may be arranged around the circumference of the measurement apparatus 102 and positioned to emit ultrasound energy radially 110 in order to obtain a cross-sectional representation of the vascular pathway 104 and the surrounding anatomy. When the sensors 106 are positioned near the area to be imaged, the control circuitry selects one or more IVUS transducers to transmit an ultrasound pulse that is reflected by the vascular pathway 104 and the surrounding structures. The control circuitry also selects one or more transducers to receive the ultrasound echo signal. By stepping through sequences of transmit-receive sets, the medical sensing system 100 system can synthesize the effect of a mechanically scanned transducer element without moving parts.

In one embodiment, the sensors 106 are disposed circumferentially around a distal portion of the measurement apparatus 102. In another embodiment, the sensors 106 are contained within the body of the measurement apparatus 102. In other embodiments, the sensors 106 are disposed radially across the measurement apparatus 102, on a movable drive member connected to the measurement apparatus 102, or on one or more planar arrays connected to the measurement apparatus 102. More examples of sensor placement are shown in FIGS. 1C and 1D.

In some embodiments, the processing engine 134, which may be included in the console 116, combines the imaging data acquired from both the IVUS and photoacoustic modalities into a single visualization. This use of both IVUS and photoacoustic modalities may provide a number of advantages over traditional systems using a single modality. First, the addition of photoacoustic sensors may allow for higher resolution mapping than traditional IVUS methods alone. Second, the combination of IVUS and photoacoustic modalities may allow for faster imaging speeds than OCT imaging or other methods. Third, the combination may allow for two-dimensional and/or three-dimensional imaging of the tissue surrounding vascular pathways. Fourth, the use of photoacoustic imaging may expand the diagnostic scope of an IVUS mapping procedure by including more of the surrounding tissue. In particular, the combined IVUS and photoacoustic mapping can allow for detection of certain types of cancers, tissue damage, and the mapping of multiple vascular pathways without sacrificing the dependability of ultrasound in detecting plaques, stenosis, and other forms of vascular diseases. Fifth, combining these two modalities may allow substantial costs savings because existing IVUS systems may be adapted to mapping systems using both modalities. Sixth, due to the interaction of optical pulses with tissue and the omni-directional emission of photoacoustic waves from the tissue, an optical pulse need not be emitted along the same axis as the transducer. This allows for more flexibility in carrying out combined photoacoustic and IVUS procedures, and may allow for precise mapping procedures even along deep or convoluted vascular pathways. Seventh, the mapping capabilities of the present disclosure may be integrated with some forms of laser therapy. For example, diagnosis of diseases in tissue may be accomplished using the optical emitter in diagnostic mode. After a diagnosis, the optical emitter can be switched to a treatment mode. In this regard, the map of the vasculature and surrounding tissue may be used to guide the application of the treatment. After the optical treatment is finished, the optical emitter can be switched back to diagnostic mode to confirm treatment of the diseased portion of tissue.

Sensor data may be transmitted via a cable 112 to a Patient Interface Module (PIM) 114 and to console 116, as well as to the processing engine 134 which may be disposed within the console 116. Data from the one or more sensors 106 may be received by a processing engine 134 of the console 116. In other embodiments, the processing engine 134 is physically separated from the measurement apparatus 102 but in communication with the measurement apparatus (e.g., via wireless communications). In some embodiments, the processing engine 134 is configured to control the sensors 106. Precise timing of the transmission and reception of signals may be used to map vascular pathways 104 in procedures using both IVUS and photoacoustic modalities. In particular, some procedures may involve the activation of sensors 106 to alternately transmit and receive signals. In systems using one or more IVUS transducers that are configured to receive both photoacoustic and ultrasound signals, the processing engine 134 may be configured to control the state (e.g., send/receive) of one or more transducers during the mapping of the vascular pathway and surrounding tissue.

Moreover, in some embodiments, the processing engine 134, PIM 114, and console 116 are collocated and/or part of the same system, unit, chassis, or module. Together the processing engine 134, PIM 114, and/or console 116 assemble, process, and render the sensor data for display as an image on a display 118. For example, in various embodiments, the processing engine 134, PIM 114, and/or the console 116 generates control signals to configure the sensor 106, generates signals to activate the sensor 106, performs amplification, filtering, and/or aggregating of sensor data, and formats the sensor data as an image for display. The allocation of these tasks and others can be distributed in various ways between the processing engine 134, PIM 114, and the console 116.

Sill referring to FIG. 1A, a pullback device 138 may be connected to the measurement apparatus 102. In some embodiments, the pullback device 138 is configured to pull a measurement apparatus 102 through a vascular pathway 104. The pullback device 138 may be configured to pull the measurement apparatus at one or more fixed velocities and/or fixed distances. In other instances, the pullback device 138 may be configured to pull the measurement apparatus at variable speeds and/or variable distances. The pullback device 138 may be selectively connected to the measurement apparatus 102 by mechanical connections such as male/female plug interactions, mechanical couplings, fasteners, and/or combinations thereof. Further, in some instances the pullback device 138 may be mechanically coupled and/or integrated with the PIM 114. In such instances, connection of the measurement apparatus 102 to the PIM 114 can couple the pullback device 138 to the measurement apparatus 102. The pullback device 138 may be slid across a cable, track, wire, or ribbon. In some embodiments, the pullback device 138 is in communication with one or more of a processing engine 134, a PIM 114, or a console 116. Furthermore, the pullback device 138 may be controlled by signals sent through a processing engine 134, a PIM 114, or a console 116. The pullback device 138 may also be placed in communication with another motivation device such as an actuator to drive an external optical emitter. In some embodiments, an actuator is synched with the pullback device 138 to synchronously move an external optical emitter and a measurement apparatus 102.

In addition to various sensors 106, the measurement apparatus 102 may include a guide wire exit port 120 as shown in FIG. 1A. The guide wire exit port 120 allows a guide wire 122 to be inserted towards the distal end in order to direct the member 102 through a vascular structure (i.e., the vascular pathway) 104. Accordingly, in some instances the measurement apparatus 102 is a rapid-exchange catheter. Additionally or in the alternative, the measurement apparatus 102 can be advanced through the vascular pathway 104 inside a guide catheter 124. In an embodiment, the measurement apparatus 102 includes an inflatable balloon portion 126 near the distal tip. The balloon portion 126 is open to a lumen that travels along the length of the IVUS device and ends in an inflation port (not shown). The balloon 126 may be selectively inflated and deflated via the inflation port. In other embodiments, the measurement apparatus 102 does not include balloon portion 126.

Figure 1B:
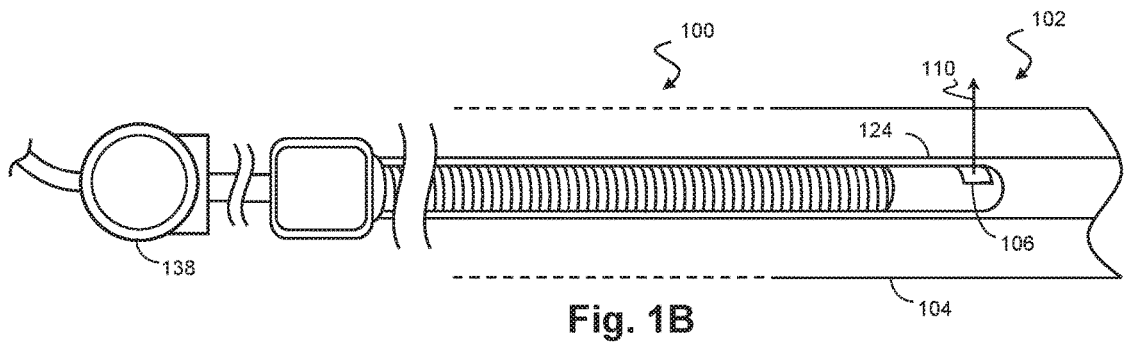
FIG. 1B is a diagrammatic schematic view of a medical sensing system according to some embodiments of the present disclosure.
Figure 1C:
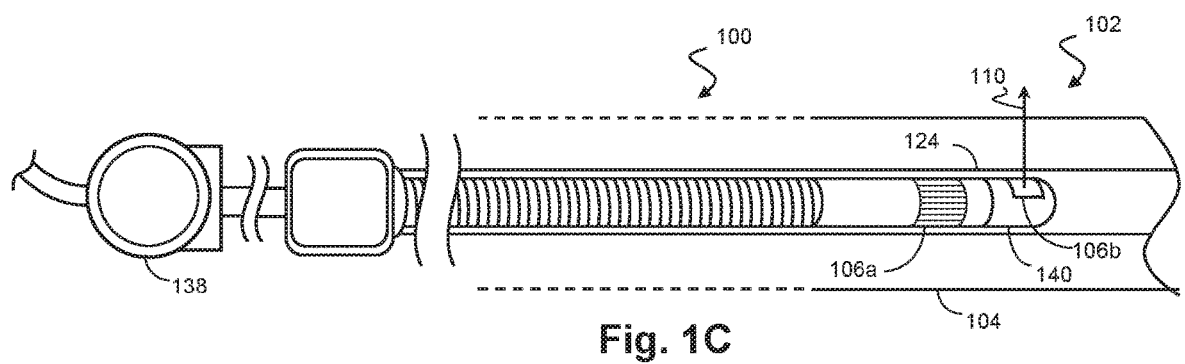
FIG. 1C is a diagrammatic schematic view of a medical sensing system with an exemplary sensor array according to some embodiments of the present disclosure.
Figure 1D:
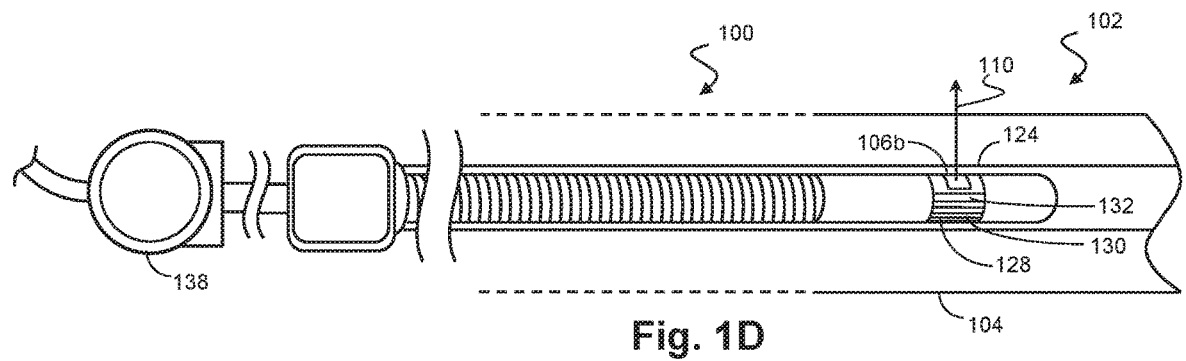
FIG. 1D is a diagrammatic schematic view of a medical sensing system with another exemplary sensor array according to some embodiments of the present disclosure.

FIG. 1B is a schematic view of a system that includes an alternative measurement apparatus 102 according to some embodiments of the present disclosure. The measurement apparatus 102 of FIG. 1B is typical of a rotational device such as a rotational IVUS ultrasound system and the one or more sensors 106 include one or more IVUS transducers arranged to emit ultrasound energy in a radial direction 110, as well as one or more photoacoustic transducers. Again, a single transducer may serve as both an IVUS transducer and a photoacoustic transducer. In such an embodiment, the one or more sensors 106 may be mechanically rotated around a longitudinal axis of the measurement apparatus 102 to obtain a cross-sectional representation of the vascular pathway 104. The system of FIG. 1B may include aspects of rotational IVUS devices, systems, and methods associated with the Revolution® catheter available from Volcano Corporation as well as those described in U.S. Pat. Nos. 5,243,988, 5,546,948, and 8,104,479 and/or U.S. patent application Ser. No. 14/837,829, filed Aug. 27, 2015, each of which is hereby incorporated by reference in its entirety.

FIGS. 1C and 1D show further examples of a measurement apparatus 102 as contemplated by the present disclosure. In particular, the composition and placement of sensors 106 may be varied on the measurement apparatus 102. For example, FIG. 1C shows a measurement apparatus 102 which includes solid-state sensors 106a (also known as phased array sensors) and a rotational sensor 106b. In the example of FIG. 1C, the rotational sensor 106b is disposed on a drive member 140 that is attached to the measurement apparatus 102. Sensors 106 may include IVUS transducers, IVUS emitters, photoacoustic transducers, and optical emitters. The rotational sensor 106b may include an optical emitter or an ultrasound transducer. In some embodiments, the drive member 140 is attached to the measurement apparatus 102 with a drive shaft or movable hinge. The drive member 140 may be configured to rotate with respect to a longitudinal axis of the measurement apparatus 102. In some cases, the solid-state sensors 106a are attached directly to the measurement apparatus 102 and remain relatively stationary with respect to the rotating drive member 140. In some embodiments, the solid-state sensors 106a are disposed circumferentially around the measurement apparatus 102. The rotational sensor 106b may be configured to rotate around the measurement apparatus 102 in full 360° arcs. Alternatively or additionally, the rotational sensor is configured to rotate in 270°, 180°, 90° arcs, or arcs of various other measurements. The direction of rotation of the rotational sensor 106b may vary along the length of the vascular pathway.

FIG. 1D shows a measurement apparatus 102 that includes a sensor array 128. In the example if FIG. 1D, the sensor array 128 may be configured to rotate with respect to a longitudinal axis of the measurement apparatus 102. In particular, the sensor array 128 may include sensors and emitters including IVUS transducers, IVUS emitters, photoacoustic transducers, and optical emitters. In some embodiments, the sensor array 128 includes sensors of at least two different types or modalities. For example, the sensor array 128 may include one or more rotational sensors 106a as well as sensors of a first type 130 and sensors of a second type 132. In the example of FIG. 1D, the sensors of the first and second types 130, 132 are disposed on the array 128 in an alternating manner. In some embodiments (not shown), sensors of the first and second types 130, 132 are disposed on the array 128 in a checkerboard configuration such that individual sensors of the first type 130 are not adjacent to each other. Additionally, sensors of the first and second types 130, 132 may take up roughly equal proportions of the area of the array 128. Although they appear as square or rectangular in the example of FIG. 1C, sensors of the first and second types 130, 132 may have circular, elliptical, polygonal, or other shapes. Sensors of the first and second types 130, 132 may be spaced across the measurement apparatus 120 or they may be placed flush against each other. In some embodiments, each type of sensor may take up roughly equal proportions of the area of the array 128 relative to the other sensor types. In other embodiments, the ratio of the surface areas of two or more sensor types on the sensor array 128 is 20% and 80%, 30% and 70%, or 40% and 60%, respectively.

In the example of FIG. 1D, a sensor array 128 is shown with sensors of two or more different types 130, 132 disposed in alternating rows. These rows may be disposed radially and may extend part way or completely around the measurement apparatus 102. In some embodiments, rows of sensors placed in a staggered formation such that the ends of individual rows are not co-terminus. In some embodiments, rows of sensors are placed adjacent to each other with no space in between. Alternatively, rows of sensors are spaced across the measurement apparatus 102 with space therebetween. In some cases, 2, 3, 4, or 5 rows of alternating sensors are disposed on the measurement apparatus 102. As discussed above, the array 128 may be configured to rotate around an axis of the measurement apparatus 102.

As the measurement apparatus 102 is moved along a vascular pathway 104, the rotational sensors 106b and the sensors of the first and second types 130, 132 may be operable to image and/or map different sections of the interior of the vascular pathway. In some embodiments, the measurement apparatus 102 is moved at a slow speed so that sensors on opposite sides of the sensor array 128 are able to map the entire vascular pathway 104 individually, creating a multi-modal map of the vascular pathway 104.

The sensor array 128 may also be disposed on a separate instrument in contact with the measurement apparatus 102, as shown in FIG. 1C. For example, the sensor array 128 may be disposed circumferentially on a drive member 140 which is in contact with the measurement apparatus 102 and revolves about the longitudinal axis of the measurement apparatus 102.

The systems of the present disclosure may also include one or more features described in U.S. Provisional Patent Application Nos. 62/315,117, 62/315,220, 62/315,275, and/or 62/315,176, each of which is filed on the same day herewith and incorporated by reference in its entirety.

Figure 2:
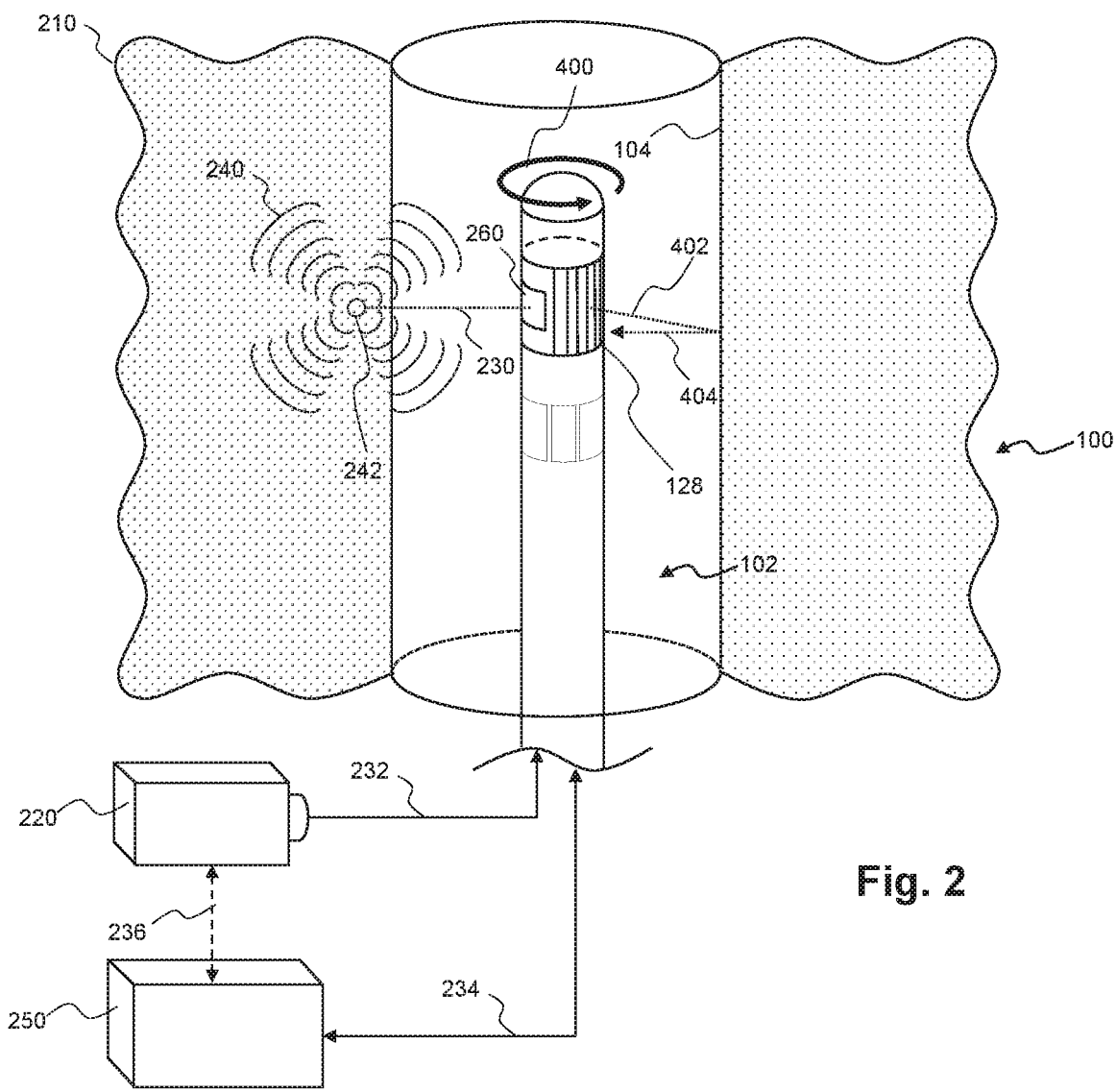
FIG. 2 is a diagrammatic, perspective view of a vascular pathway and surrounding tissue with an instrument positioned within the vascular pathway according to an embodiment of the present disclosure.

FIG. 2 is a diagrammatic, perspective view of a vascular pathway 104 and surrounding tissue 210 with a measurement apparatus 102 such as that depicted in FIG. 1A, 1B, 1C, or 1D disposed within the vascular pathway 104. In some embodiments, the measurement apparatus 102 is connected to and moved through the vascular pathway 104 by a pullback device 138 such as that depicted in FIGS. 1A and 1B. A sensor array 128 may be disposed around the measurement apparatus 102. In some embodiments, the sensor array 128 includes a plurality of ultrasound transducers which emit ultrasound signals 402 radially toward a section of the wall of the vascular pathway 104. The ultrasound signals 402 are reflected off the wall of the vascular pathway 104 and travel back toward the measurement apparatus 102 as ultrasound echo signals 404. These ultrasound echo signals 404 may be received by ultrasound transducers on the sensor array 128. In some cases, a communication system 250 controls the transducers of the sensor array 128 to emit ultrasound signals 402 and receive ultrasound echo signals 404. In some embodiments, the medical sensing system 100 is operable to map the vascular pathway 104 by mapping sections 406 of the pathway wall as the measurement apparatus 102 is advanced through the vascular pathway 104 in direction 400.

The sensor array 128 may be configured to rotate around a longitudinal axis of the measurement apparatus 102. In the example of FIG. 2, a top section of the measurement apparatus 102 with the sensor array 128 may be rotated in a direction 400. The speed and direction of the rotation may vary throughout a medical procedure. For example, the direction of rotation may be changed several times to allow the measurement apparatus to obtain extra diagnostic data on an area of interest. In some embodiments, sections of the measurement apparatus 102 are disposed within a sheath 124 such as that depicted in FIG. 1B in order to protect the measurement apparatus 102 or vascular pathway.

An optical emitter 220 is also shown emitting optical pulses 230 toward an area of interest within the tissue. In some embodiments, the area of interest includes part of a vascular pathway 104 as well as adjacent tissue. In some embodiments, the optical emitter 220 is a laser source that emits short laser pulses toward the area of interest. The optical emitter 220 may be placed outside the vascular pathway 104. In the example of FIG. 2, the optical emitter 220 is disposed outside the vascular pathway 104 and routes a series of optical pulses 230 to the measurement apparatus 102. In some embodiments, the optical pulses 230 are routed along an optical fiber to the measurement apparatus 102. The optical pulses 230 may then be emitted through an emitter element 260 disposed on or within the measurement apparatus 102. Additionally or alternatively, an optical emitter 220 may be configured to be placed within the vascular pathway 104. In this case, the optical emitter 220 may send a signal through connection 234 to an emitter element 260 located on the measurement apparatus 102, which in turn emits optical pulses 230 into the area of interest.

The optical pulses 230 may interact with the tissue 210 at a focus 242, generating a series of photoacoustic waves 240 that propagate through the tissue 210 and the vascular pathway 104. The photoacoustic waves 240 are received by sensors in the sensor array 128 connected to the measurement apparatus 102. In some embodiments, the sensor array 128 is configured to send and receive signals to image and/or map the vascular pathway. The measurement apparatus 102 may be moved through the vascular pathway 104 in order to image and/or map the vascular pathway 104. In some cases, the sensor array 128 is configured to map the vascular pathway 104 independently of the photoacoustic waves 240 by transmitting ultrasound signals toward the vessel walls and receiving the corresponding reflected ultrasound echo signals.

In the example of FIG. 2, the optical emitter 220 is in communication with a communication system 250 via connection 236. In some embodiments, the communication system 250 is the processing engine 134, the PIM 114, or the console 116 of FIG. 1A. The communication system 250 may also be connected to the measurement apparatus 102 via connection 234. Furthermore, the measurement apparatus 102 may be in direct communication with the optical emitter 220 via connection 232. In some embodiments, connections 232, 234, and 236 are cables capable of transmitting electronic or optical signals. Furthermore, connection 232 may be a microcable, connection 234 may be an optical fiber, and connection 236 may be a wireless connection such as a Bluetooth or WiFi connection. Additionally, the optical emitter 220 may include a wireless signal receiver. Connection 234 may also operate to power the measurement device 102 including the sensor array 128.

Still referring to FIG. 2, the communication system 250 may coordinate the operation of the optical emitter 220 and the sensors of the sensor array 128 by sending signals to synchronize the emission of optical pulses 230 and the reception of photoacoustic signals by the sensor array 128. In some cases, the communication system 250 coordinates the operation of different sensor types on the sensor array 128. In particular, the communication system 250 may switch between ultrasound and photoacoustic modalities on the sensor array 128. The operation of only one type of sensor at a time may filter out noise and yield more accurate mapping of the vascular pathway.

Figure 3:
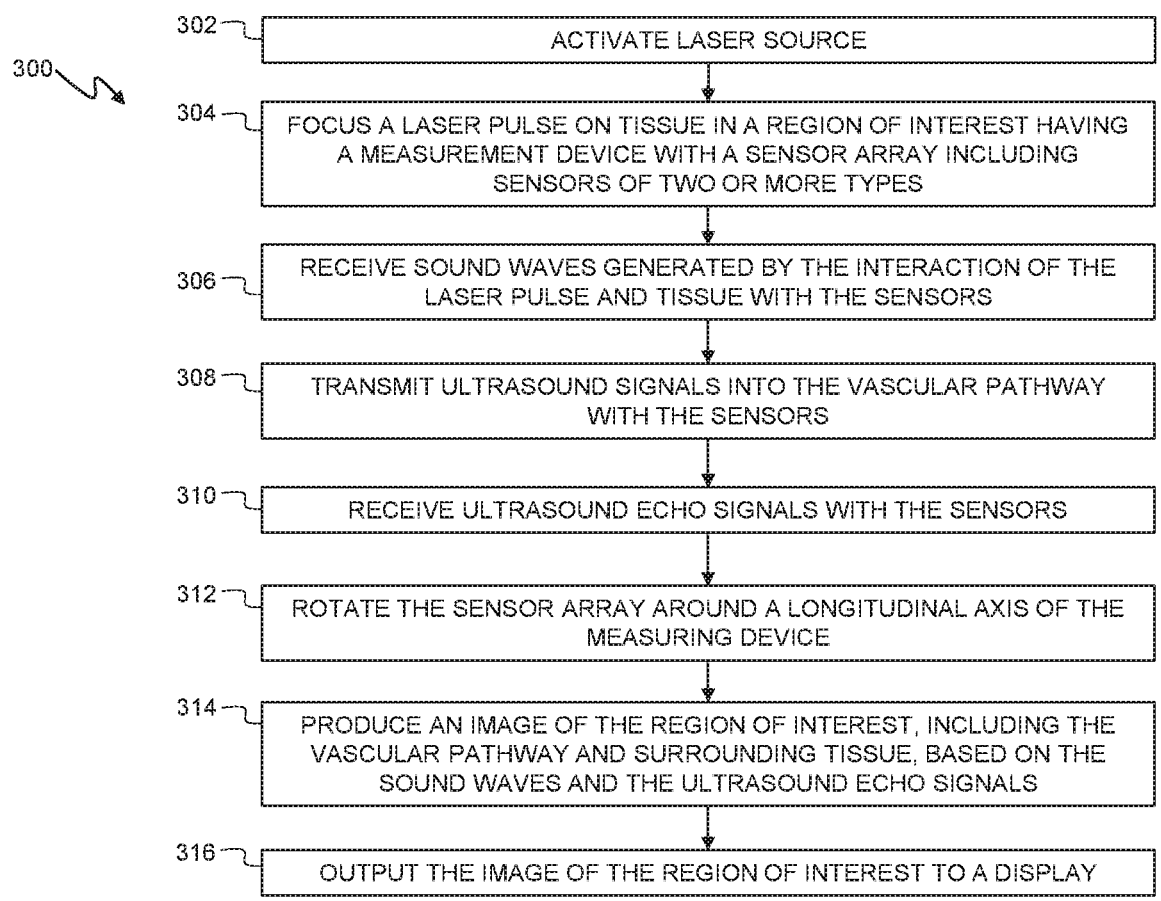
FIG. 3 is a flow diagram of a method for mapping a vascular pathway with a transducer array according to some embodiments of the present disclosure.

FIG. 3 is a flow chart showing a method 300 of mapping an area of interest using both photoacoustic and IVUS modalities. It is understood that additional steps can be provided before, during, and after the steps of method 300, and that some of the steps described can be replaced or eliminated for other embodiments of the method. In particular, steps 304, 306, 308, 310, and 312 may be performed simultaneously or in various sequences as discussed below.

At step 302, the method 300 can include activating a laser source. This laser source may be the optical emitter 220 of FIG. 2. In some embodiments, the laser source is disposed externally and is in communication with a laser emitter disposed on a measurement device within a vascular pathway. In this case, the external laser source may transmit laser pulses through a communication device, such as an optical fiber, to the measurement device. In some cases, the laser source is activated by a communication system 250 by means of an electronic or optical signal. This signal may be sent wirelessly, and the external laser source may be equipped with a wireless signal receiver. Alternatively, the laser source may be included on a transducer array disposed on or within the measurement device.

At step 304, the method 300 can include focusing a laser pulse on tissue in a region of interest having a measurement device with a sensor array including sensors of two or more types. In some embodiments, the region of interest includes a portion of tissue including a portion of at least one vascular pathway 104. The measurement device may be disposed within the vascular pathway 104. The region of interest may be chosen based on a suspected or diagnosed problem in the tissue, or based on the proximity of a region of tissue to problems within a vascular pathway 104. In other embodiments, the region of interest is part of a more general mapping plan. For example, a mapping plan for a section of a vascular pathway 104 may involve the mapping of tissue surrounding the vascular pathway 104 along its length. The interaction of the emitted laser pulse and tissue in the region of interest creates a number of photoacoustic waves 240 that emanate from the tissue.

In some embodiments, the measurement device is the measurement apparatus 102 depicted in FIGS. 1A, 1B, 1C, 1D, and 2. In some embodiments, the transducer array is the sensor array 128 depicted in FIGS. 1A, 1B, 1C, 1D, and 2. The transducer array may include one or more sensors and emitters including IVUS transducers, photoacoustic transducers, optical emitters, and optical receivers. The two or more transducer elements may be arranged in any of the examples depicted in FIGS. 1A, 1B, 1C, 1D, and 2. In some embodiments, the transducer array is a solid-state array or a phased array that does not rotate as it travels through the vascular pathway 104. In other embodiments, the transducer array is a rotational array disposed on a revolving portion of the measurement device. In some embodiments, the transducer array is disposed circumferentially around the measurement device. The interaction of the emitted laser pulse and tissue in the region of interest creates a number of photoacoustic waves 240 that emanate from the tissue.

At step 306, the method 300 can include receiving sound waves generated by the interaction of the laser pulse and tissue with the sensors. In some cases, the sensors can function with the traditional IVUS functionality to receive ultrasound waves. In other cases, some or all of the sensors are dedicated to receive photoacoustic waves. In some embodiments, the sensors are controlled by a communication system 250 like that depicted in FIG. 2. In another embodiment, a processing engine 134 or a PIM 114 may control the operation of the sensors of the sensor array 128. Signals may be sent from processing engine 134 or the PIM 114 to the sensors via connector 234, causing the sensors to receive diagnostic information such as sound waves, ultrasound signals, and ultrasound echo signals.

At step 308, the method 300 can include transmitting ultrasound signals into the vascular pathway 104 with at least one transducer element. In some embodiments, the at least one transducer of step 308 is an ultrasound transmitter. The ultrasound signals may be transmitted toward the walls of the vascular pathway 104 from the one or more transmitters. The transmitted ultrasound signals may be deflected off the walls of the vascular pathway 104 and propagate through the vascular pathway 104 as ultrasound echo signals.

At step 310, the method 300 can include transmitting ultrasound signals into the vascular pathway 104 with the sensors. Ultrasound signals may be transmitted toward the walls of the vascular pathway 104 and may be deflected off the walls of the vascular pathway 104 and propagate through the vascular pathway 104 as ultrasound echo signals.

Steps 304, 306, 308, and 310 may be coordinated in the method 300 and occur in various orders based on the desired outcome of a medical procedure. For example, transmission of ultrasound signals and reception of ultrasound echo signals can occur at regular intervals throughout the method 300, while reception of photoacoustic waves may occur sporadically. This may be the case in a medical procedure to map a vascular pathway 104 and spot-check trouble areas of tissue surrounding sections of the vascular pathway 104. Alternatively, steps 304, 306, 308, and 310 are performed successively. For example, steps 304, 306, 308, and 310 may be performed successively before proceeding to the next step to avoid signal noise and allow for adequate signal processing. This may be useful when method 300 is used in a system where a photoacoustic sensor and an ultrasound transducer are each included in a sensor array. Furthermore, the steps of method 300 may be interleaved in various orders.

At step 312, the method 300 can include rotating the sensor array about a longitudinal axis of the measurement device. In some embodiments, the sensor array is rotated throughout steps 304, 306, 308, and 310, as in the case where the measurement device continually maps a vascular pathway as is it pulled through the vascular pathway. In other embodiments, the sensor array is kept motionless during the steps 304, 306, 308, and 310, and then rotated before these steps are carried out again. The rotation of the sensor array may be accomplished through the use of a drive member connected to the measurement device. In some embodiments, such as the example of FIG. 1C, parts of the sensor array are rotated around a longitudinal axis of the measurement device while other parts of the sensor array are not rotated. The rotation of the sensor array can vary in direction and rate of rotation. For example, the sensor array may be rotated 180° in a counter-clockwise direction and/or rotated in a 180° counter-clockwise direction. Rotations in each direction of 90°, 270°, 360°, and other angles are also contemplated.

At step 314, the method 300 can include producing an image of the region of interest, including the vascular pathway 104 and surrounding tissue, based on the sound waves and the ultrasound echo signals. In some embodiments, a processing engine (such as the processing engine 134 of FIG. 1A) in communication with the transducer array produces the image of the region of interest. This image can include both two-dimensional and three-dimensional images based on the received sensor data. In some cases, the image includes a number of two-dimensional cross sections of the vascular pathway 104 and surrounding tissue.

At step 316, the method 300 includes outputting the image of the region of interest to a display 118. This display 118 can include a computer monitor, a screen on a patient interface module (PIM) 114 or console 116, or other suitable device for receiving and displaying images.

In an exemplary embodiment within the scope of the present disclosure, the method 300 repeats after step 316, such that method flow goes back to step 304 and begins again. Iteration of the method 300 may be utilized to map a vascular pathway and surrounding tissue.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical sensing device comprising:
   an elongate body sized and shaped for insertion into a vascular pathway;
   a rotational drive member extending along a length of the elongate body;
   an optical emitter coupled to a distal portion of the rotational drive member, the optical emitter configured to emit optical pulses to tissue in a region of interest; and
   a measurement apparatus coupled to the distal portion, wherein the measurement apparatus comprises at least one ultrasound transducer element,
   wherein the at least one ultrasound transducer element is configured to:
      receive sound waves generated by the tissue as a result of interaction of the optical pulses with the tissue;
      transmit ultrasound signals; and
      receive ultrasound echo signals based on the transmitted ultrasound signals,
   wherein the optical emitter and the at least one ultrasound transducer element are disposed on opposite sides of the distal portion such that the optical emitter and the at least one ultrasound transducer element are longitudinally co-located along a length of the rotational drive member, and
   wherein the optical emitter is configured to emit the optical pulses to the tissue while the optical emitter is proximate to the tissue and the at least one ultrasound transducer element is configured to receive the sound waves generated by the tissue while the at least one ultrasound transducer element is proximate to the tissue such that the rotational drive member is configured to rotate from a first orientation in which is the optical emitter is proximate to the tissue to a second orientation in which the at least one ultrasound transducer element is proximate to the tissue between the optical emitter emitting the optical pulses to the tissue and the at least one ultrasound transducer element receiving the sound waves generated by the tissue.

2. The medical sensing device of claim 1, further comprising a processing engine in communication with the measurement apparatus, the processing engine operable to produce an image of the region of interest based on the received sound waves and the received ultrasound echo signals.

3. The medical sensing device of claim 2, further comprising a display in communication with the processing engine, the display configured to visually display the image of the region of interest.

4. The medical sensing device of claim 1, wherein the drive member is configured to rotate the optical emitter and the at least one ultrasound transducer element around a longitudinal axis of the measurement apparatus.

5. The medical sensing device of claim 1, wherein the optical emitter is in communication with an external optical source.

6. The medical sensing device of claim 5, wherein an optical fiber connects the measurement apparatus and the external optical source.

7. The medical sensing device of claim 1, wherein the measurement apparatus comprises an array of ultrasound transducer elements configured to transmit the ultrasound signals and receive the ultrasound echo signals based on the transmitted ultrasound signals.

8. The medical sensing device of claim 1, wherein the at least one ultrasound transducer element is configured to alternate in receiving the sound waves and the ultrasound echo signals.

9. The medical sensing device of claim 1, wherein the measurement apparatus further comprises at least one photoacoustic transducer configured to receive the sound waves generated by the tissue as a result of interaction of the optical pulses with the tissue.

10. The medical sensing device of claim 9, wherein the at least one photoacoustic transducer and the at least ultrasound transducer element are configured to alternate in receiving the sound waves and the ultrasound echo signals.

11. A medical sensing system comprising:
an optical source configured to emit optical pulses;
an intravascular device in communication with the optical source, the intravascular device including:
an elongate body;
a rotational drive member extending along a length of the elongate body;
an optical emitter coupled to a distal portion of the rotational drive member, the optical emitter configured to emit the optical pulses received from the optical source to tissue in a region of interest while the optical emitter is proximate to the tissue; and
a measurement apparatus coupled to the distal portion, wherein the measurement apparatus comprises at least one ultrasound transducer element,
wherein the optical emitter and the at least one ultrasound transducer element are disposed on opposite sides of the distal portion such that the optical emitter and the at least one ultrasound transducer element are longitudinally co-located along a length of the rotational drive member,
wherein the at least one ultrasound transducer element is configured to:
while the at least one ultrasound transducer element is proximate to the tissue, receive sound waves generated by the tissue as a result of interaction of the optical pulses with the tissue;
transmit ultrasound signals; and
receive ultrasound echo signals based on the transmitted ultrasound signals;
wherein the rotational drive member is configured to rotate from a first orientation in which is the optical emitter is proximate to the tissue to a second orientation in which the at least one ultrasound transducer element is proximate to the tissue between the optical emitter emitting the optical pulses to the tissue and the at least one ultrasound transducer element receiving the sound waves generated by the tissue;
a processing engine in communication with the intravascular device, the processing engine operable to produce an image of the region of interest based on the received sound waves and the received ultrasound echo signals; and
a display in communication with the processing engine, the display configured to visually display the image of the region of interest.

12. The medical sensing system of claim 11, wherein the drive member is configured to rotate the optical emitter and the at least one ultrasound transducer element around a longitudinal axis of the measurement apparatus.

13. The medical sensing system of claim 11, further comprising an optical fiber extending between the intravascular device and the optical source.

14. The medical sensing system of claim 11, further comprising a controller operable to control the operation of the optical source and the rotation of the drive member.

15. The medical sensing system of claim 11, wherein the measurement apparatus comprises an array of ultrasound transducer elements configured to transmit the ultrasound signals and receive the ultrasound echo signals based on the transmitted ultrasound signals.

16. The medical sensing system of claim 11, wherein the at least one ultrasound transducer element is configured to alternate in receiving the sound waves and the ultrasound echo signals.

17. The medical sensing system of claim 11, wherein the measurement apparatus further comprises at least one photoacoustic transducer configured to receive the sound waves generated by the tissue as a result of interaction of the optical pulses with the tissue.

18. A method of mapping a region of interest, comprising:
transmitting, with a laser emitter of an intravascular device positioned within a vascular pathway of a region of interest, focused laser pulses to tissue in the region of interest while the laser emitter is proximate to the tissue;
receiving with at least one transducer element of the intravascular device positioned within the vascular pathway of the region of interest, sound waves generated by interaction of the focused laser pulses with the tissue while the at least one transducer element is proximate to the tissue,
wherein the laser emitter and the at least one transducer element are coupled to a rotational driver member of the intravascular device,
wherein the laser emitter and the at least one transducer element are disposed on opposite sides of the rotational drive member such that the laser emitter and the at least one transducer element are longitudinally co-located along a length of the rotational drive member;
rotating, with the drive member, the laser emitter and the at least one transducer element about a longitudinal axis of the intravascular device, wherein the rotational drive member rotates from a first orientation in which is the laser emitter is proximate to the tissue to a second orientation in which the at least one transducer element is proximate to the tissue between the laser emitter emitting the focused laser pulses to the tissue and the at least one transducer element receiving the sound waves generated by the tissue;
producing an image of the region of interest based on the received sound waves; and
outputting the image of the region of interest to a display.

19. The medical sensing device of claim 1, wherein the optical emitter and the at least one ultrasound transducer element are collectively disposed around a complete circumference of the elongate body.

20. The method of claim 18, wherein the at least one transducer element comprises a photoacoustic sensor.

* * * * *